(12) United States Patent
Howard et al.

(10) Patent No.: US 8,197,417 B2
(45) Date of Patent: Jun. 12, 2012

(54) METABOLIC ANALYZER TRANSDUCER

(75) Inventors: C. Peter Howard, Humboldt, TN (US); Joel Grimes, Tecumseh, MI (US)

(73) Assignee: Medical Graphics Corporation, St. Paul, MN (US)

( * ) Notice: Subject to any disclaimer, the term of this patent is extended or adjusted under 35 U.S.C. 154(b) by 1135 days.

(21) Appl. No.: 12/042,158

(22) Filed: Mar. 4, 2008

(65) Prior Publication Data

US 2009/0227887 A1 Sep. 10, 2009

(51) Int. Cl.
*A61B 5/08* (2006.01)
(52) U.S. Cl. ......... 600/532; 600/529; 600/531; 600/534
(58) Field of Classification Search ......................... None
See application file for complete search history.

(56) References Cited

U.S. PATENT DOCUMENTS

| | | | |
|---|---|---|---|
| 4,440,177 A | 4/1984 | Anderson et al. | 128/719 |
| 4,463,764 A | 8/1984 | Anderson et al. | 128/719 |
| 4,572,208 A | 2/1986 | Cutler et al. | 128/718 |
| 4,621,929 A * | 11/1986 | Phillips | 374/43 |
| 4,957,107 A * | 9/1990 | Sipin | 128/204.21 |
| 5,043,576 A | 8/1991 | Broadhurst et al. | 250/293 |
| 5,060,656 A | 10/1991 | Howard | 128/718 |
| 5,117,674 A | 6/1992 | Howard | 73/31.07 |
| 5,178,155 A | 1/1993 | Mault | 128/718 |
| 5,179,958 A | 1/1993 | Mault | 128/718 |
| 5,363,857 A | 11/1994 | Howard | 128/718 |
| 5,789,660 A | 8/1998 | Kofoed et al. | |
| 5,948,512 A | 9/1999 | Kubota et al. | |
| 6,174,289 B1 * | 1/2001 | Binder | 600/532 |
| 6,206,837 B1 | 3/2001 | Brugnoli | 600/529 |
| 6,232,370 B1 | 5/2001 | Kubota et al. | |
| 6,277,645 B1 | 8/2001 | Mault | 436/133 |
| 6,309,360 B1 | 10/2001 | Mault | 600/531 |
| 6,312,389 B1 | 11/2001 | Kofoed et al. | |
| 6,325,978 B1 | 12/2001 | Labuda et al. | |
| 6,402,698 B1 | 6/2002 | Mault | 600/532 |
| 6,468,222 B1 | 10/2002 | Mault et al. | 600/531 |
| 6,478,736 B1 | 11/2002 | Mault | |
| 6,485,138 B1 | 11/2002 | Kubota et al. | |
| 6,506,608 B2 | 1/2003 | Mault | 436/133 |

(Continued)

FOREIGN PATENT DOCUMENTS

WO   WO 91/18279   * 11/1991

OTHER PUBLICATIONS

Law et al. Electronic transducer for rumination research. Journal of Animal Science, vol. 41, 1975, pp. 213-218.*

(Continued)

*Primary Examiner* — Russell S Negin
(74) *Attorney, Agent, or Firm* — Nikolai & Mersereaus, P.A.; Thomas J. Nikolai

(57) ABSTRACT

A compact and wearable metabolic analyzer transducer comprising a housing containing a plurality of analog sensors, an A/D converter, a microcontroller, and a power source operatively coupled thereto where the microcontroller is programmed to compute minute ventilation, $O_2$ uptake, and $CO_2$ production of a subject. The transducer and its contents are of a size and weight that can either be easily supported from a facemask worn by a subject or incorporated in a respiratory circuit. The measured values can be wirelessly transmitted or transmitted, via a cable, to a remote personal computer, a personal digital assistant (PDA), or other display devices such as digital watches or image projectors.

64 Claims, 10 Drawing Sheets

U.S. PATENT DOCUMENTS

| | | | |
|---|---|---|---|
| 6,571,200 B1 | 5/2003 | Mault | 702/182 |
| 6,572,561 B2 | 6/2003 | Mault | 600/532 |
| 6,599,253 B1 | 7/2003 | Baum et al. | |
| 6,612,306 B1 | 9/2003 | Mault | 128/204.22 |
| 6,616,615 B2 | 9/2003 | Mault | 600/531 |
| 6,616,896 B2 | 9/2003 | Apperson et al. | |
| 6,620,106 B2 | 9/2003 | Mault | 600/532 |
| 6,629,934 B2 | 10/2003 | Mault et al. | 600/538 |
| 6,645,158 B2 | 11/2003 | Mault | 600/532 |
| 6,718,982 B2 | 4/2004 | Smith et al. | 128/207.12 |
| 6,740,033 B1 * | 5/2004 | Olejniczak et al. | 600/301 |
| 6,790,178 B1 | 9/2004 | Mault et al. | |
| 6,806,113 B2 * | 10/2004 | Miyama et al. | 438/31 |
| 6,815,211 B1 | 11/2004 | Blazewicz et al. | |
| 6,899,683 B2 | 5/2005 | Mault et al. | 600/531 |
| 6,899,684 B2 | 5/2005 | Mault et al. | 600/531 |
| 6,955,650 B2 | 10/2005 | Mault et al. | 600/531 |
| 6,955,652 B1 | 10/2005 | Baum et al. | |
| 7,108,659 B2 | 9/2006 | Ross et al. | 600/529 |
| 7,335,164 B2 | 2/2008 | Mace et al. | |
| 7,805,975 B2 * | 10/2010 | Howard et al. | 73/1.07 |
| 2002/0026937 A1 | 3/2002 | Mault | 128/200.24 |
| 2002/0138213 A1 | 9/2002 | Mault | 702/32 |
| 2003/0023180 A1 | 1/2003 | Mault | 600/531 |
| 2003/0023181 A1 | 1/2003 | Mault | 600/532 |
| 2003/0023182 A1 | 1/2003 | Mault et al. | 600/532 |
| 2003/0065275 A1 | 4/2003 | Mault et al. | 600/531 |
| 2003/0152607 A1 | 8/2003 | Mault | 424/439 |
| 2004/0013570 A1 | 1/2004 | Labuda et al. | |
| 2004/0186389 A1 | 9/2004 | Mault et al. | 600/531 |
| 2004/0199083 A1 | 10/2004 | Mault | 600/532 |
| 2007/0016381 A1 * | 1/2007 | Kamath et al. | 702/19 |
| 2007/0225612 A1 | 9/2007 | Mace et al. | |
| 2008/0000476 A1 * | 1/2008 | Richey et al. | 128/204.21 |

OTHER PUBLICATIONS

Chou et al. Study on the osmotic pre-treatment and infrared radiation on drying kinetics and colour changes during drying of agricultural products. ASEAN Journal on Science and Technology for Development. vol. 18, 2001, pp. 11-23.*

Wilmore, J. H., and Costill, D.L., "Adequacy of the Haldane transformation in the computation of exercise Vo$_2$ in man", Journal of Applied Physiology, vol. 35, No. 1, Jul. 1973, pp. 85-89.

Robinson, G. J. B., Peyton, P.J., Terry, D., Malekzadeh, S., and Thompson, B., "Continuous measurement of gas uptake and elimination in anesthetized patients using an extractable marker gas", Journal of Applied Physiology, vol. 97, Apr. 2004, pp. 960-966, 22 pages.

International Search Report and Written Opinion for International Application No. PCT/US2009/035981, 7 pages, 2009.

* cited by examiner

METABOLIC ANALYZER TRANSDUCER

BACKGROUND OF THE INVENTION

1. Field of the Invention

The present invention relates generally to respiratory gas analysis and, more particularly, to a lightweight, small size, self-contained metabolic rate transducer capable of being carried by a facemask of a subject at rest or undergoing physical activity or incorporated in a respiratory circuit.

2. Discussion of the Prior Art

All of the processes taking place in the body ultimately result in the production of heat. Heat production and caloric consumption or metabolism can be viewed in a similar context. Indirect calorimetry is a practical means by which heat production is measured to quantify metabolic rate or function.

All energy production or metabolism in the body ultimately depends on the utilization of oxygen. Indirect calorimetry involves directly measuring the consumption of oxygen ($O_2$) and the production of carbon dioxide ($CO_2$) through quantitative analysis of inspired and expired air flow, oxygen, and carbon dioxide to provide an accurate measure of energy metabolism. Energy production or metabolism measurement through indirect calorimetry at rest and during activity is used by physicians for clinical reasons, by coaches to measure athletic performance, and by trainers to measure fitness levels. There are many different gas analysis techniques used in the prior art of indirect calorimetric, some of which only estimate oxygen consumption since they lack the ability to directly measure carbon dioxide production which is necessary to account for the difference in inhaled and exhaled air flow of the subject. This compromised approach, many times an attempt to reduce size, weight, cost, and complexity of the apparatus or to circumvent the challenges of gas transport from the subject to the sensor itself results in poor accuracy and less repeatable measures of metabolism. Further, these abbreviated methods fail to account for intersubject variations because they rely on assumptions made from population averages.

It has been known for some time the analysis of a subject's respiration provides valuable information relating to the physical condition of the subject. The four most commonly measured variables are: (1) respiratory volume; (2) oxygen consumption; (3) carbon dioxide production; and (4) respiratory exchange ratio (RER), which is the ratio of carbon dioxide produced to oxygen consumed. One of the earliest efforts to conduct indirect metabolic rate analysis involved the use of a so-called Douglas Bag. A Douglas Bag metabolic analysis technique involved the timed collection of expired breath in a rubberized bag, measuring the volume of expired gas collected and analyzing the gas composition contained within the rubberized bag for $O_2$ and $CO_2$ content. Metabolic rates were then calculated from the data obtained. The Douglas Bag technique was time consuming, subject to error and could only be performed on relatively stationary subjects in well-equipped laboratories. Also, this technique was not well-suited to the measurement of short-duration transients in metabolic functions.

Since the data obtained from respiratory gas analysis is so valuable in diagnosing cardiopulmonary dysfunction and evaluating overall cardiovascular fitness, intense effort has been directed towards the development of simpler and faster automated metabolic analyzers. The intense interest in physical fitness and aerobic exercise, such as running, has helped to focus further effort in this field. Various instruments are presently available for the determination of the total volume of respired air from a subject being studied. These devices include spirometers, plethysmographs, and pneumotachographs. Numerous instruments are also available for determining $O_2$ and $CO_2$ content in respired gas. Some of the more recent techniques involve the use of a discrete zirconium oxide ($ZrO_2$) sensor and a non-dispersive infrared (NDIR) gas analyzer for determining $CO_2$ content. A metabolic analyzer of the type described is disclosed in U.S. Pat. No. 4,463,764 to Anderson, et al. While such instruments are accurate, they are large, heavy, and require frequent calibration as well as special operating skills. An instrument described in the Anderson et al. patent is so large a fixed equipment rack incorporates all of it and it can only be used in a clinical or laboratory setting.

U.S. Pat. No. 5,363,857 to Howard describes a metabolic rate analyzer having a $CO_2$ detector, an $O_2$ detector, a flow resistance, a differential pressure transducer, a solenoid-actuated metering valve for producing a volumetrically-proportional sample of respired gas, a vacuum regulator for receiving the sample, a pump for drawing the sample from the vacuum regulator and a processor for periodically sampling the differential pressure signal to provide a flow signal, to modulate power applied to the solenoid-actuated flow proportioning valve and to provide a measure of the total volume of respired gas. The processor in the Howard analyzer is programmed to correlate the total volume of respired gas, $O_2$ content, and $CO_2$ content to provide a measure of metabolic rate.

While the apparatus described in the Howard '857 patent is of a reduced size when compared to the earlier Anderson equipment and can be worn on the body for ambulatory applications is not miniaturized to the point where it can be an integral part of a facemask assembly, as well as not being able to provide true breath by breath analysis. Adding to the weight and bulk of the Howard apparatus is the reliance upon solenoid-operated metering valves and an electromechanical pump for moving respiratory gas through $O_2$ and $CO_2$ analyzers.

U.S. Pat. No. 6,955,650 to Mault et al. describes a portable device for measuring the metabolic rate of an individual including a respiratory gas flow path containing a hygiene barrier capable of blocking a predetermined pathogen possibly present in exhaled gases. The flow pathway is contained within the interior of an outer housing and includes a flow tube leading to a flow meter and an oxygen sensor. The device further includes a "computation unit" utilizing the outputs from the flow meter and the oxygen sensor to determine metabolic rate. Carbon dioxide production is computed rather than measured and this can lead to significant inaccuracies in establishing the true metabolic rate of the subject and the true substrate utilization.

While the Mault et al. '650 patent indicates a $CO_2$ sensor may be incorporated into the device so as to directly measure, rather than calculate, $CO_2$ concentrations, it fails to teach how such a device can be configured so as to be sufficiently small and lightweight to be incorporated into a metabolic analyzer able to be supported on a subject's facemask.

It is accordingly one aspect of the present invention to provide novel, non-invasive, lightweight, small size metabolic analyzers that can either be carried by a facemask worn by a subject or incorporated in a respiratory circuit and accurately providing output signals corresponding to a subject's metabolic rate and respiratory exchange ratio and gas concentrations on a real-time, breath-by-breath basis.

Still another aspect of the invention is to provide a metabolic analyzer incorporating a removable, lightweight optical guide incorporating both an open channel mainstreamed sample chamber of $CO_2$ detection and an orifice plate for establishing a pressure drop and subsequent flow analysis using a differential pressure transducer.

Another aspect of the invention is to provide a new and improved metabolic analyzer weighing in the range of 10 to 3 oz. and possibly less than 5 oz.

Another aspect of the invention is to provide a metabolic analyzer especially constructed for use in a health club setting or for personal use for providing basic metabolic information on which a work-out prescription can be structured either for optimizing weight loss (fat burning) or cardiorespiratory conditioning.

SUMMARY OF THE INVENTION

The foregoing aspects and advantages are achieved by providing a transducer for housing a plurality of detectors including, but not limited to, respiratory gas analyzers, a flow sensor, an absolute temperature sensor, an analog-to-digital converter connected to receive electrical output signals from the above-mentioned detectors and a microcontroller circuit coupled to the analog-to-digital converter and a battery power supply, all of these components and a battery power supply being contained in a housing of a small size and lightweight adapted to be operatively coupled to a subject whose metabolic rate is being measured.

In some embodiments, a unitary lightweight transducer may include one or more of the following features: (a) a housing having a tubular socket with a central lumen, (b) an oxygen sensor mounted to the housing and exposed to the lumen for producing a first electrical signal proportional to inspired and expired oxygen, (c) a diatomic gas sensor contained in the housing including an arcuate, open channel having a concave wall with a reflective surface thereon and first and second ends, the first end aligned with an IR source and the second end aligned with an IR detector for producing a second electrical signal proportional to the concentration of a predetermined gas in inspired and expired respiratory air flowing through the transducer, (d) a flow sensor exposed to respiratory gas flow in the lumen for producing a third electrical signal proportional to the respiratory gas flow, the oxygen sensor, diatomic gas sensor and the flow sensor aligned with a mainstream respiratory gas flow path through the lumen, (e) an analog-to-digital converter connected to receive the first, second and third electrical signals, (f) a microcontroller circuit coupled to the analog-to-digital converter, said oxygen sensor, diatomic gas sensor, flow sensors, analog-to-digital converter and microcontroller circuit being contained in a housing of a size and weight is adapted to be supported on the face of a subject whose oxygen uptake and carbon dioxide production are to be measured, (g) an absolute temperature sensor affixed to the detector mounting structure and exposed to respiratory air passing through the tubular socket, past the detector mounting structure and through the optical waveguide member, (h) a second printed circuit substrate having the microcontroller circuit affixed thereto, the second substrate being disposed in a second space between the outer shell and the tubular socket of the housing, (i) a power supply disposed in the housing and operatively coupled to the analog-to-digital converter and the microcontroller circuit, j) a wireless transmitter disposed in the housing and coupled to the microcontroller circuit for sending computed values of oxygen uptake and carbon dioxide production to a remote receiver, and (k) a serial data input channel on the microcontroller adapted to receive heart rate signals from an external heart rate sensor over a wireless communications link.

In some embodiments, a lightweight respiratory gas concentration transducer may include one or more of the following features: (a) a tubular housing having a respiratory gas flow channel extending from a proximal end to a distal end of said housing, (b) a diatomic gas detector module disposed in said housing in alignment with the gas flow channel, said detector module having an optical waveguide member with an arcuate, open groove with a concave wall, the concave wall having a reflective surface thereon and said groove having first and second ends, the first end aligned with an IR source and the second end aligned with an IR detector, the open groove adapted to receive samples of inspired and expired air from a subject on whom the transducer is attached, (c) an oxygen sensor mounted on the detector module and exposed to respiratory gas flowing through the gas flow channel, (d) a flow sensor in the housing for measuring the volume rate of flow of respiratory gas through the flow channel, (e) a temperature measuring device and a barometric pressure sensor affixed to the housing, (f) a dc power supply disposed in the tubular housing for providing power to the IR source, the IR detector, the oxygen sensor and the temperature sensor, and (g) a microcontroller disposed in the housing and connected to the IR source, the IR sensor, the oxygen sensor, the temperature sensor, the dc power supply, the flow sensor and the barometric pressure sensor for computing the subject's oxygen uptake and carbon dioxide production on a breath-by-breath basis.

In some embodiments, a metabolic analyzer transducer may include one or more of the following features: (a) a housing capable of being coupled to a facemask and comfortably worn by a subject, (b) an analog sensor located within the housing, (c) a microcontroller located within the housing capable of receiving inputs from the analog sensor and compute $CO_2$ production by the subject, (d) a power source located within the housing operatively coupled to the microcontroller, (e) an $O_2$ sensor located within the housing, (f) a wireless transmitter located within the housing, (f) a respiratory gas analyzer within the housing, (g) a flow sensor within the housing, (h) an absolute temperature sensor within the housing, and (i) an analog-to-digital converter capable of receiving inputs from any of the sensors within the housing.

In some embodiments, a metabolic analyzer transducer system may include one or more of the following features: (a) a metabolic analyzer transducer able to sense and compute $CO_2$ production by a subject, (b) a facemask for operably coupling the metabolic analyzer transducer to the subject, (c) a user interface communicatively coupled to the metabolic analyzer transducer, (d) a ergometer, (e) a wireless connection communicatively coupling the metabolic analyzer transducer with the user interface, (f) a wireless connection device housed on the metabolic analyzer transducer for communicatively coupling the metabolic analyzer transducer with the user interface, (g) a sensor housed by the metabolic analyzer transducer for detecting $CO_2$, and (h) a microcontroller housed in the metabolic analyzer transducer capable of receiving inputs from the $CO_2$ sensor.

In some embodiments, a method of manufacturing a metabolic analyzer transducer may include one or more of the following steps: (a) molding an outer plastic shell having a bottom wall, a top wall and a side wall joining the top wall to the bottom wall and defining a hollow chamber where the bottom wall and top wall each include a centrally disposed aperture, (b) placing a detector mounting structure in the hollow chamber, the detector mounting structure having a base with a central aperture concentrically aligned with the apertures in the top wall and bottom wall and with a tubular socket projecting outward of the base, (c) inserting an optical waveguide member within said tubular socket, the optical waveguide member having a tubular sidewall and a base containing said arcuate, open channel and an orifice of a predetermined shape and size in the base, and where a portion of the tubular sidewall of the optical waveguide member extends through the aperture in the top wall, (d) inserting an oxygen sensor for producing a first electrical signal proportional to inspired and expired oxygen into the central aperture, (e) attaching a diatomic gas sensor to the detector mounting structure, the diatomic gas sensor including said arcuate, open channel said channel having a concave wall with a reflective surface thereon and first and second ends, the first end aligned with an IR source and the second end aligned with an IR detector for producing a second electrical signal proportional to the concentration of a predetermined gas in inspired and expired respiratory air flowing through the orifice, (f) attaching a flow sensor to the detector mounting structure, the flow sensor producing a third electrical signal proportional to a pressure drop across said orifice, the oxygen sensor, diatomic gas sensor and the flow sensor aligned with a mainstream respiratory gas flow path, (g) coupling an analog-to-digital converter to the detector mounting structure, the analog-to-digital converter connected to receive the first, second and third electrical signals, and (h) coupling a microcontroller circuit to the detector mounting structure, the microcontroller circuit coupled to the analog-to-digital converter, said oxygen sensor, diatomic gas sensor, flow sensors, and analog-to-digital converter.

In some embodiments, a method of manufacturing a lightweight respiratory gas concentration transducer may include one or more of the following steps: (a) molding a tubular housing having a respiratory gas flow channel extending from a proximal end to a distal end of said housing, (b) placing a diatomic gas detector module in said housing in alignment with the gas flow channel, said detector module having an optical waveguide member with an arcuate, open groove with a concave wall, the concave wall having a reflective surface thereon and said groove having first and second ends, the first end aligned with an IR source and the second end aligned with an IR detector, the open groove adapted to receive samples of inspired and expired air from a subject on whom the transducer is attached, (c) mounting an oxygen sensor on the detector module and exposing to respiratory gas flowing through the gas flow channel, (d) forming an orifice in a base of the optical waveguide member for measuring a pressure drop across said base due to gas flow through said orifice, (e) affixing a temperature measuring device and a barometric pressure sensor to the housing, (f) inserting a dc power supply in the tubular housing for providing power to the IR source, the IR detector, the oxygen sensor and the temperature sensor, (g) inserting a microcontroller in the housing, and (h) connecting the microcontroller to the IR source, the IR sensor, the oxygen sensor, the temperature sensor, the dc power supply, the flow sensor and the barometric pressure sensor for computing the subjects oxygen uptake and carbon dioxide production on a breath-by-breath basis.

In some embodiments, a method of measuring a metabolic rate of a subject may include one or more of the following steps: (a) measuring $CO_2$ with an analog sensor located within a housing coupled to a facemask, (b) receiving inputs from the analog sensor at a microcontroller and computing $CO_2$ production by the subject, the microcontroller located within the housing, (c) powering the analog sensor and microcontroller with a power source located within the housing operatively coupled to the microcontroller and analog sensor, (d) measuring $O_2$ with an $O_2$ sensor located within the housing, (e) transmitting measured physiological values of the subject with a wireless transmitter located within the housing, (f) transferring physiological values of the subject to a remote device via a wireless connection, (g) measuring air flow with a flow sensor located within the housing, (h) measuring respired air from the subject with a respiratory gas analyzer located within the housing, (i) measuring temperature with an absolute temperature sensor located within the housing, (j) zeroing a flow transducer during each breath, (k) zeroing $CO_2$, (l) spanning $O_2$ on a breath by breath basis, (m) correcting an $O_2$ signal from flow to yield a pressure compensated $O_2$ output, and (n) augmenting the $O_2$ signal to provide real-time breath by breath measurements and removal of DC drift.

DESCRIPTION OF THE DRAWINGS

The foregoing features, aspects and advantages of the invention will become apparent to those skilled in the art from the following detailed description of an embodiment, especially when considered in conjunction with the accompanying drawings in which like numerals in the several views refer to corresponding parts.

DESCRIPTION OF THE PREFERRED EMBODIMENT

Figure 1:
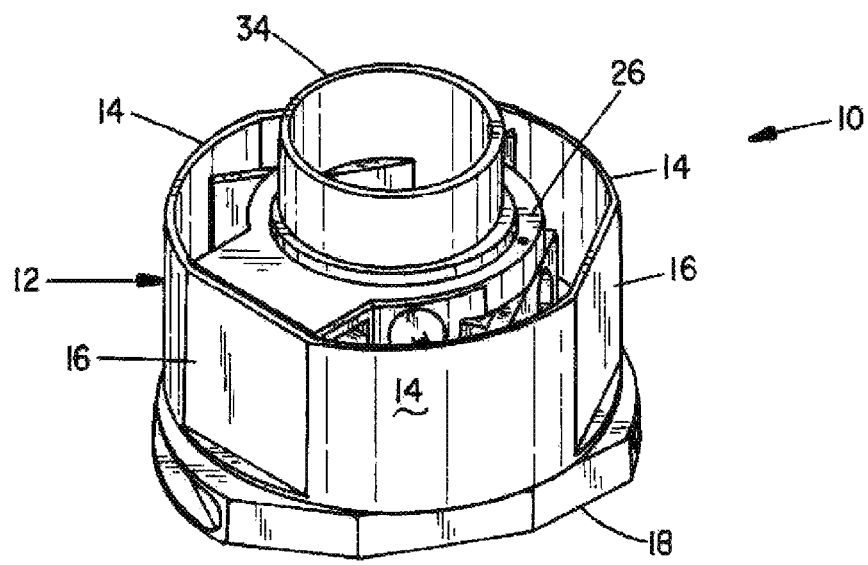
FIG. 1 is a perspective view of the metabolic analyzer transducer made in accordance with the present invention and with its cover removed to show interior construction.

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

Referring first to FIG. 1, there is indicated generally by numeral 10 an embodiment of the metabolic analyzer transducer of the present invention in its assembled form, but with its cover removed so internal parts can be viewed. It is seen to comprise an outer molded plastic shell or housing 12 of a somewhat hexagonal-shaped cross-section having three slightly rounded side faces 14 separated by three planar faces 16. The shell 12 has a base 18 of a predetermined thickness dimension secured thereto.

Figure 2:
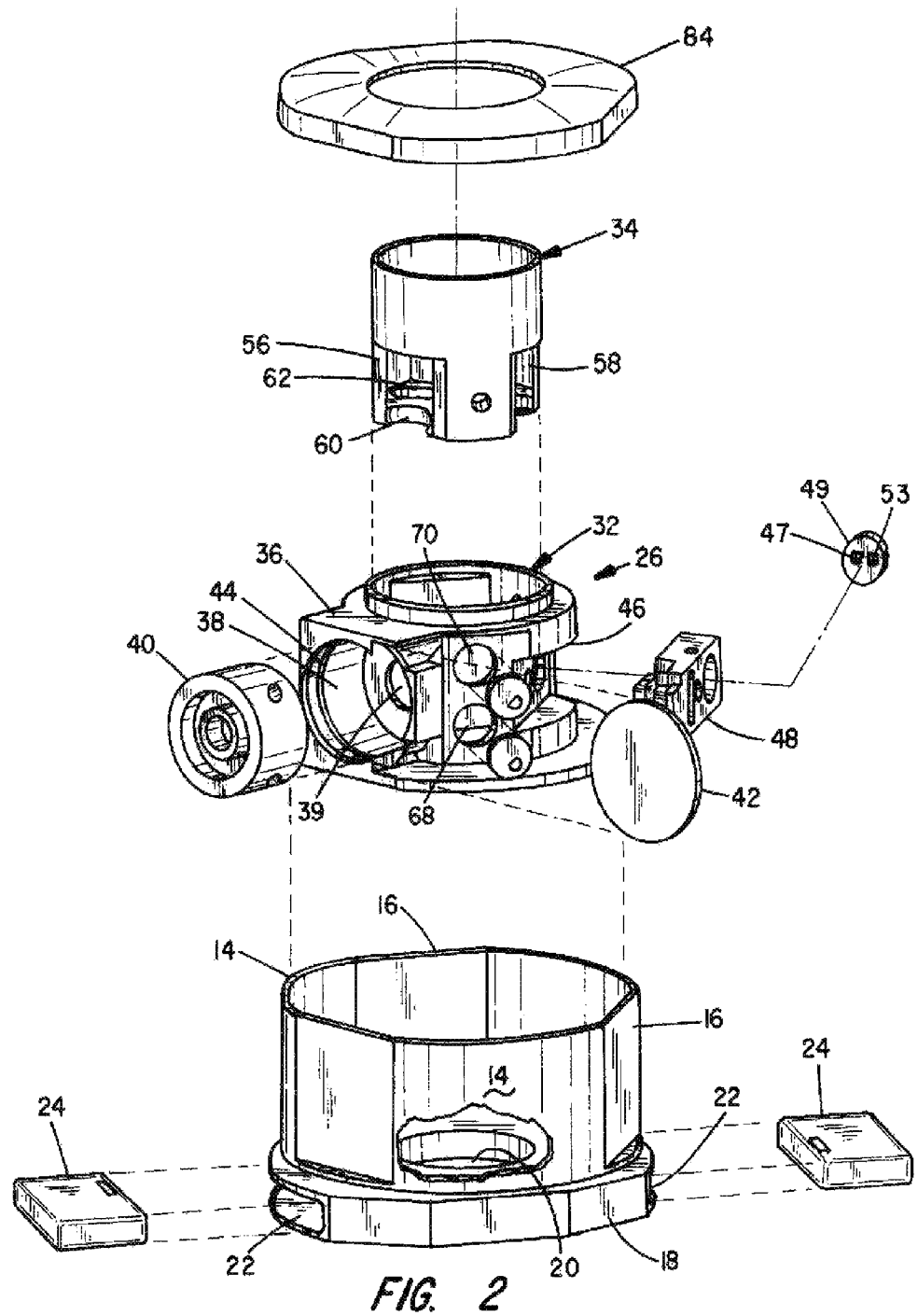
FIG. 2 is an exploded view of the device of FIG. 1.

Referring next to FIG. 2, it can be seen there is provided in the base member 18 a centrally disposed circular aperture 20 for receiving a multiapertured flow diffuser (not shown) promoting a generally laminar flow to respiratory gases. The base also includes a pair of slots 22 adapted to receive rechargeable batteries 24 therein. As will be explained in greater detail below, the batteries provide a voltage source for electronic circuits and other electrical components comprising the transducer 10.

Figure 3:
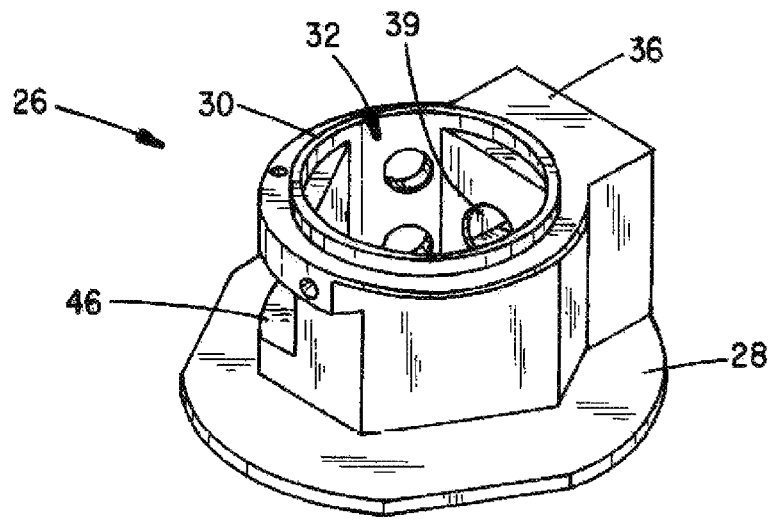
FIG. 3 is a perspective view of the detector housing of FIG. 2.

The shell 12 is designed to contain a detector housing indicated generally by numeral 26 shown in greater detail in FIG. 3. The detector housing comprises a molded plastic part especially designed to contain an oxygen sensor, a differential pressure sensor and a carbon dioxide sensor, all of which are designed to fit within the confines of the molded plastic shell 12. More particularly, the detector housing 26 has a flat, planar base 28 with a peripheral contour for fitting closely to the inside surface of the walls 14 and 16 of the shell 12.

Integrally formed with and supported on the base 28 of the detector housing 26 is a socket member 30 having a cylindrical cavity 32 adapted to receive an optical guide member 34 therein. Projecting radially from the wall defining the cavity 32 is a block-like extension 36 having a circular aperture 38 formed therethrough and leading to the cavity 32. The aperture 38 is dimensioned to receive therein an $O_2$ sensor 40. Formed in an end wall of the cylindrical socket member 30 is an aperture 39 leading to the interior of the cavity 32.

The oxygen sensor 40 preferably comprises a galvanic fuel cell, although other types of oxygen sensors may also be used. Galvanic oxygen sensors are absolute so zero output equals 0% oxygen which is an advantage in calibration. Augmentation provides response times in the order of 150 milliseconds for a 90% step change. The sensors also are comparatively low cost. As those skilled in the art appreciate, a galvanic cell oxygen sensor is a diffusion-limited, metal/air battery. The oxygen in a gas sample diffuses through a diffusion barrier in the cell and reaches a cathode electrode. Here, it is reduced to hydroxyl ions which, in turn, pass through an electrolyte to oxidize a metal anode. A current, proportional to the rate of consumption of oxygen, is generated when the cathode/anode circuit is completed, the cell operating in what is virtually a short-circuit condition. Since the rate at which oxygen reaches a cathode is limited by the diffusion barrier, the cell current is a direct function of this rate. This, in turn, is a direct function of the concentration of oxygen in the sample. An alternative sensor would be one using Pulsed Fluorescence Quenching. This type sensor is naturally very fast, very small and light and accurate. A pulsed blue light emitter causes a polymer film to fluoresce. The excited fluorophores are reduced in intensity and pulse duration by the amount of oxygen present known as quenching. Oxygen concentration is directly proportional to the quenching effect. The oxygen sensor 40 is exposed to the respiratory gas stream flowing as a subject inhales and exhales.

Another embodiment allows for a pulse fluorescence quenching oxygen sensor. When a specific polymer coating is exposed to a blue light pulse, the excited fluorescence or fluorophores collide with the oxygen molecules present. This results in a quenching of the fluorescent intensity and a reduction in its duration. This effect is directly proportional to the concentration of oxygen present. Measurement is achieved by comparing the intensity and duration of the outgoing blue pulse with the resulting fluorescence. Since this effect is virtually instantaneous, sensors produce response times of a few milliseconds. The polymer coatings are not permanent which means the sensors have a useful but not everlasting life. This type of detector would perform well in a wearable metabolic analyzer transducer.

With continued reference to FIG. 2, the oxygen sensor 40 is held in place by a thin, circular disk 42 when it is inserted into a C-shaped groove 44 formed in the wall of the block 36.

Figure 4:
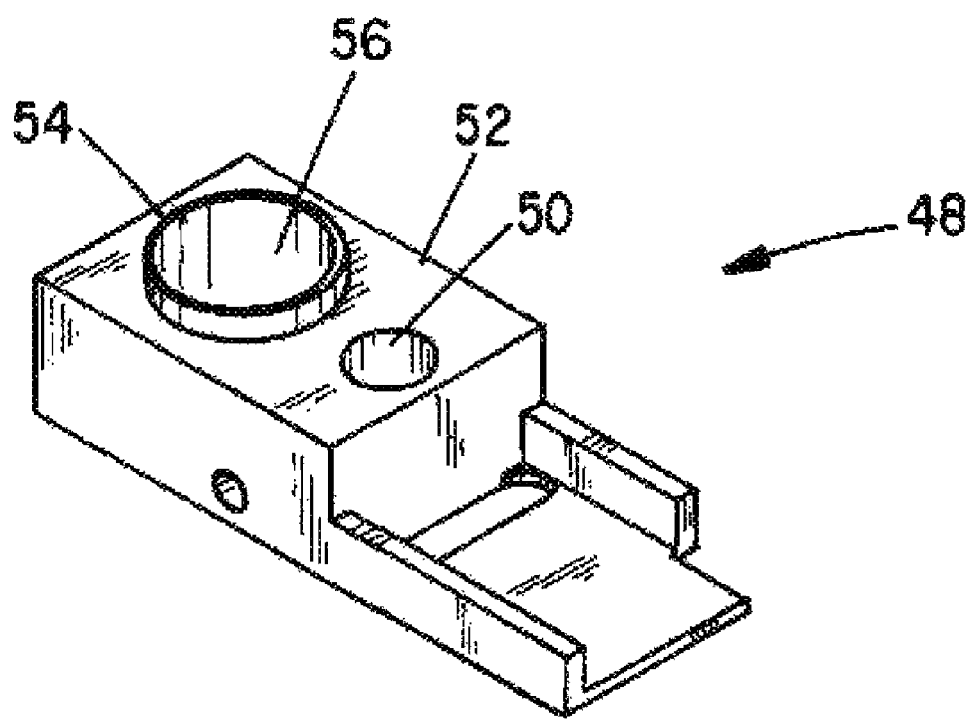
FIG. 4 is a perspective view of the thermal block of FIG. 2.

Still with reference to FIGS. 2 and 3, it will be seen the detector housing 26 has a slot 46 extending inward from the outer periphery of a vertical wall surface. This slot 46 is adapted to receive a thermal block member 48 in it. A perspective view of the thermal block member 48 is illustrated in FIG. 4 hereof. Bores 50 and 51 are formed inwardly of a block portion 52 of the device 48 and each is adapted to contain a source of infrared energy, such as an incandescent bulb or other IR source, therein. In relatively close proximity to the bore 50 is a further bore 54 in which is disposed an infrared sensor or detector 56. As will be described further, the combination of the IR source located in the bore 50 and the IR detector 56, when properly oriented with respect to an open sided, arcuate sample chamber having reflected walls, comprises a non-dispersive infrared (NDIR) carbon dioxide sensor. No focusing optics is required, thus reducing power consumption.

The optical guide member 34 preferably comprises a molded, lightweight, non-thermally conductive plastic, thin-walled cylindrical tube having three symmetrically arranged cutouts or windows. Only two such windows 57, 58 are visible in the exploded view of FIG. 2. Extending inwardly from the three windows and formed in the base 66 of optical guide member 34 are generally semicircular open-path recesses 60 and these recesses each have an arcuate, concave wall profile as at 62 in FIG. 2 disposed between upper and lower abrupt edges. Because of this construction, i.e., the optical sample chamber with its abrupt edges, there is rapid washout of respiratory gases passing through it normal to its axis of energy conduction. This concave surface is provided with a very thin (1000 Å) highly polished gold coating, such as may be provided by vapor depositing, sputtering or electrochemically depositing a thin layer of the highly reflective metal on the exposed surfaces. While other metals may be used, gold is helpful because of its inertness, low IR absorption, and resistance to tarnishing.

When the optical guide member 34 is appropriately placed in the socket 32 of the detector housing 26, one end of one of the three reflective light guides 62 is aligned with the IR source 50 in the thermal block 48 and other end of the same reflective, arcuate light channel is directly adjacent the IR sensor 56. While only one of the three available arcuate light channels is used at a time in implementing a NDIR $CO_2$ sensor, the other two provide symmetry to the guide member 30 and also permits substitution of a clean reflective sample chamber should the one in use become dirty by merely rotating member 34 in its socket to align a clean channel with the IR source and detector. It is also contemplated the otherwise spare sample chambers can be used to sense other trace gases if appropriate, wavelength sources and detectors are used in association therewith. Also, helpful to the design is the very thin coating on the non-thermally conductive substrate allows some absorption of IR energy and attendant localized warming of the gold layer minimizing condensation and clouding of the reflective surface. The sharp abrupt edges of the arcuate recesses aid in the rapid filling and removal of respiratory gases from the sample chamber(s) during inspiratory and expiratory cycles.

In an additional embodiment, infra-red detection can be improved with regard to signal stability and amplification by the use of a dual detector. The detector can consist of two thermopile 49 hot junctions referenced to a single cold junction. Intercepting the energy striking each hot junction can be two optical band pass filters 47 and 53 of different wavelengths. One is at the wavelength of interest, 4.26 microns for CO2, and the other at a wavelength which is neutral density and would be unresponsive to any other gases in the sample. In most cases the filter center frequency is 3.92 microns. The detector's hot junctions are nominally 0.0025" square and 0.06" apart center to center. The detector can be mounted as with a single detector close to the energy emission from the guide and with the sensing junction and filter being just off the center axis of the energy emitting from the guide towards the outer curved edge of the guide when looking down. The neutral density filter and hot junction would be 'in-board' and still in the energy beam.

This embodiment can allow a differential signal to be obtained and effects due to temperature, changes in the broadband energy emission thru the guide and source emissivity are largely cancelled out. As thermopile detector 49 is a temperature sensing device, it is vulnerable to temperature changes caused by the high flows through the detector housing being it is mounted in such close proximity. First order stability can be achieved by using the signal from the thermistor embedded by the detector's cold junction to allow for compensation or temperature control. The reference detector provides a much more sensitive compensation to further enhance the signal. Because two detectors are sharing one energy source, there is some reduction of signal intensity compared to this achieved with a single detector. However the benefits gained by common mode rejection signals allow for increased amplification without an increase in noise or drift.

The new metabolic system is designed to work in extreme ambient conditions by nature of its size and portability. The detection system is therefore exposed to fairly dramatic temperature fluctuations during inspired and expired breathing which increases the need for high detector stability.

An added benefit of the dual detector is it permits an alternative method for monitoring the ambient levels of the CO2 during inspiration. The extra resolution achieved at these low levels allows signals that are easily distinguished from zero drift. Because the length of the optical guide permits good resolution at these levels due to the Beer-Lambert law, small changes in span calibration have little or no effect on the signal strength.

Figure 5:
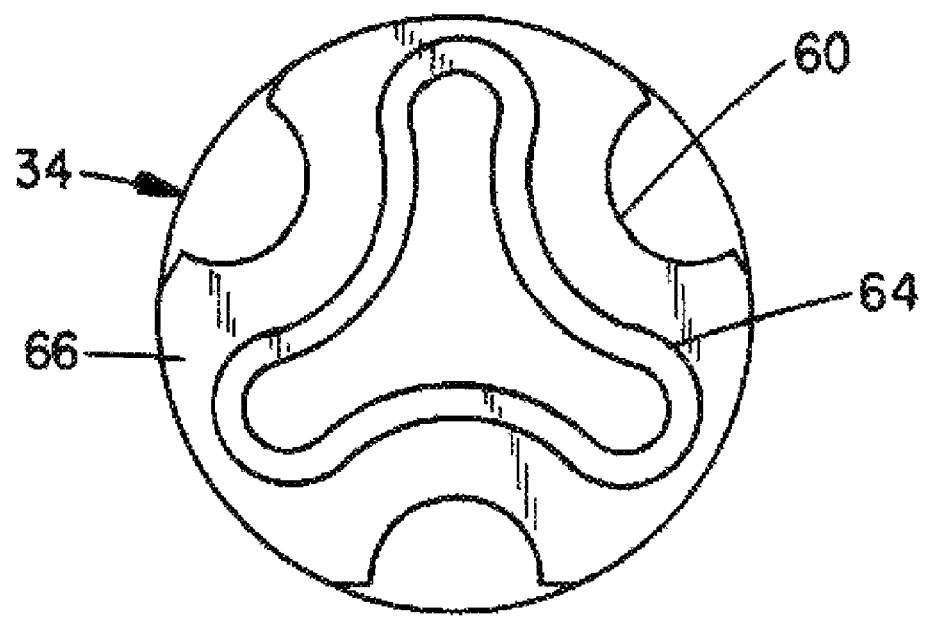
FIG. 5 is a bottom view of the optical guide of FIG. 2.
Figure 6:
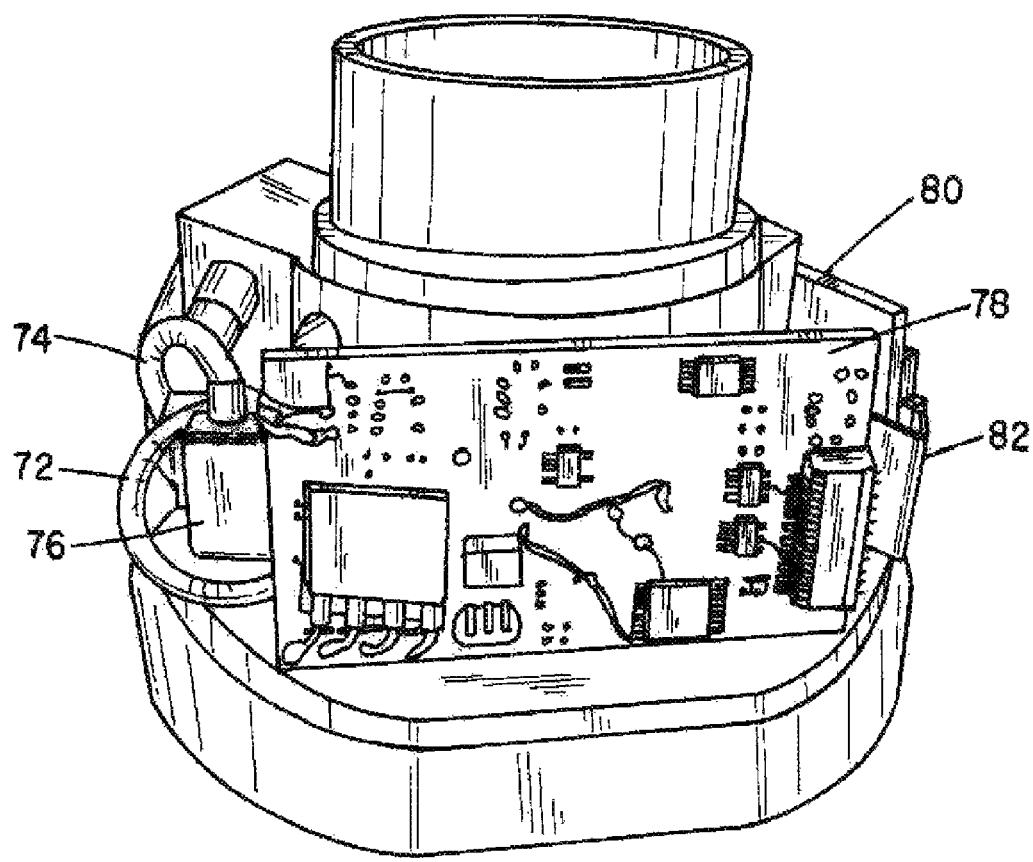
FIG. 6 is a side view with the outer shell removed showing placement of the analog circuit board and the digital circuit board on the detector block of FIG. 2.

FIG. 5 is a bottom view of the optical guide member 34. Here, one can see a symmetrically arranged three-lobed aperture 64 formed through a bottom wall 66 of the optical guide member 34. The three-lobed aperture 64 is symmetrically arranged relative to the semicircular recesses 60. When the light guide member 34 is situated within the cavity 32 of the detector housing, its base member 66 is disposed midway between pressure sensing ports 68 and 70 (FIG. 2). As seen in FIG. 6, short plastic tubes 72 and 74 extend from the ports 68 and 70 to the input ports of a solid-state differential pressure sensor 76, which is designed to provide an electrical output signal proportional to the pressure drop across the aperture 64 as respiratory gases are made to flow through the aperture 20 in the base of the outer shell through the socket 32 of the detector housing 26 and through the three-lobed aperture 64. The differential pressure sensor employed is based on piezoresistive semiconductor technology to provide a non-linear electrical output signal (later linearized in the microcontroller 104) proportional to the measured pressure differential and may comprise a Type All Sensors (5 inch D1-MV) or an equivalent thereof.

In implementing the present invention, excess heat from the infrared light sources contained in the bores 50 and 51 of the thermal block 48 is conducted to the two connection ports 68 and 70, elevating their temperature to a few degrees above ambient. This has been found to prevent condensation and, therefore, eliminates blockage of the ports otherwise arising from moisture in expired breath. Further, the pressure pickup ports on opposed sides of the aperture 64 are comprised of polyethylene 35 micron sinters having a hydrophobic coating. This prevents loss of signal from excess moisture and/or condensation blocking the transfer of pressure to the pressure transducer 76.

It will be appreciated; then, the semicircular recess aligned at its ends with the IR source and IR detector serves both as a $CO_2$ sample chamber and the orifice plate for establishing a pressure drop and subsequent flow analysis, via the differential pressure sensor. The removability of the optical guide 34 permits not only cleaning of the semicircular light guides by washing, but also allows for the substitution of a optical guide having a different size critical orifice 64 to accommodate for special high or low flow ranges.

Still referring to FIG. 6, there can be seen first and second printed circuit boards 78 and 80 disposed on edge and resting on the base 28 of the detector housing and abutting the vertical flat surfaces thereof. The printed circuit board 78 includes the analog circuitry associated with the oxygen sensor 40, the NDIR carbon dioxide detector, and the differential pressure silicon sensor 76. Also mounted on the printed circuit board 78 are a barometric pressure silicone sensor, an optional relative humidity sensor, and an absolute temperature sensor. The temperature sensor may typically comprise a semi-conductor element, e.g., a LM61 available from National Semiconductor, Inc. Other temperature sensors may be used as well.

The printed circuit board 80 is coupled to the printed circuit board 78 by a flexible flat cable member 82. Disposed on the printed circuit board 80 is an analog-to-digital converter, a microprocessor-based controller chip along with power supply circuitry derived from the batteries 24. The printed boards when mounted to the detector housing are capable of fitting within the outer shell 12. A cover 84 (FIG. 2) fits over the cylindrical light guide member 34 and is removably attached in covering relation with respect to the outer shell 12.

Because of the way in which the several sensors are physically arranged about the detector housing 26 and the use of a sample chamber that is open to a mainstream flow of respiratory gases, there is no need to provide sample tubes with optical lenses leading from the main flow channel to various sensors nor is a pump needed for circulating the respiratory gas samples to the sensors as in the prior art side streaming approaches. As such, there is no latency time between a given breath and a detector signal based on breath. This obviates the need to correlate measured flow with the detected $O_2$ and $CO_2$ sensed signals as in prior art metabolic analyzers.

Having described the mechanical construction of the metabolic analyzer transducer, attention will next be directed to the electronic circuitry and, in this regard, reference will be made to the schematic electrical block diagrams of FIGS. 7 and 8.

The present invention provides a complete, wearable, low-power (less than 0.5 watts), low-cost, processor-driven metabolic analyzer transducer providing accurate and continuous data to patients on a respirator or, at the other extreme, to individuals involved in athletic, general fitness and weight-loss training. This data includes, but is not limited to, oxygen uptake ($VO_2$), carbon dioxide production ($VCO_2$), heart rate, caloric expenditure for both fat and carbohydrates as well as maximal data for world-class athletics involved in competitive training. Data is generated on a real-time basis and can be uploaded and processed, via an interactive website, or displayed locally, via a PDA (personal digital assistant) or similar device.

As already described above, the metabolic analyzer transducer of the present invention comprises five sensing circuits (and an optional sixth) physically located around a central through-channel for the purposes of measuring breath-by-breath metabolic rate in subjects, via indirect calorimetry. In FIG. 7, the five sensing circuits necessary to measure metabolic rate accurately include a gas temperature sensor 90, a carbon dioxide detector 92, an oxygen sensor 94, sensors for measuring ventilation volume including differential pressure sensor 96 and barometric sensor pressure 98. An optional humidity sensor 100 may also be incorporated. The outputs from these various sensors are applied, via buffer amplifier circuits, each labeled "X" in FIG. 7, which allow for offset and optional gain adjustment for the several sensors. As those familiar with the signal processing arts appreciate, sensor devices commonly have a DC offset voltage for the signal of interest to ride upon and it is generally necessary to remove the offset before amplification takes place so only the signal of interest is amplified.

The outputs from the buffer circuits are fed into an analog-to-digital converter 102, which functions to digitize the offset and gain adjusted sensor output signals fed to the microcontroller 104, via a bus 106.

The microcontroller 104 may comprise an ATMEL AT91SAM7S ARM microcontroller, but other integrated circuit microcontrollers may also be used. It is used to store the offset adjustments for the individual sensors and these may be fed over the bus 106 to a digital-to-analog converter 108 to produce the actual analog control signals to the amplifier circuits so when the analyzer is booted up, stored default values for the offset and gain adjustments will become available to the amplifiers.

Figure 7A:
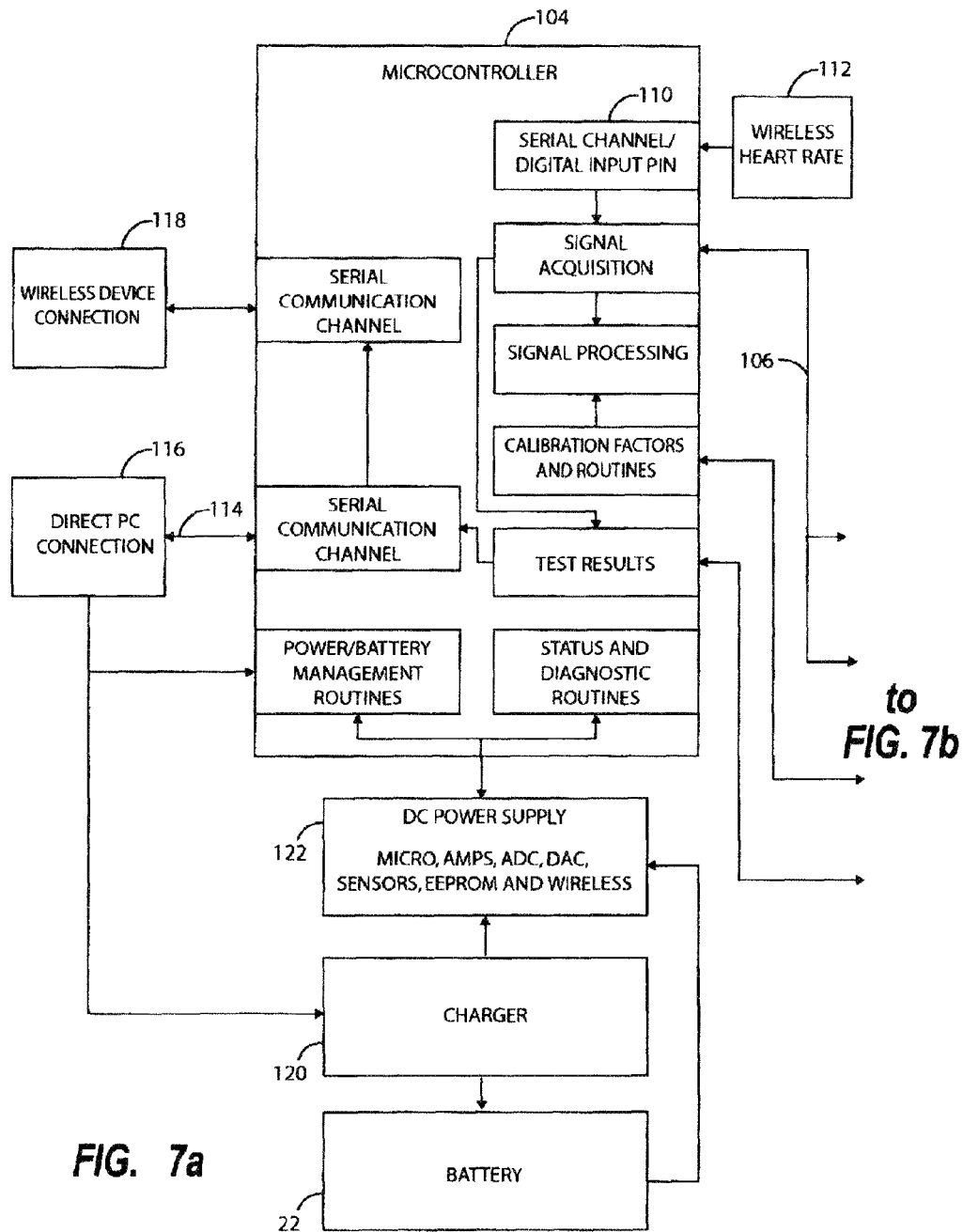
FIG. 7 is a block diagram of the electronic circuitry employed in implementing the present invention.
Figure 7B:
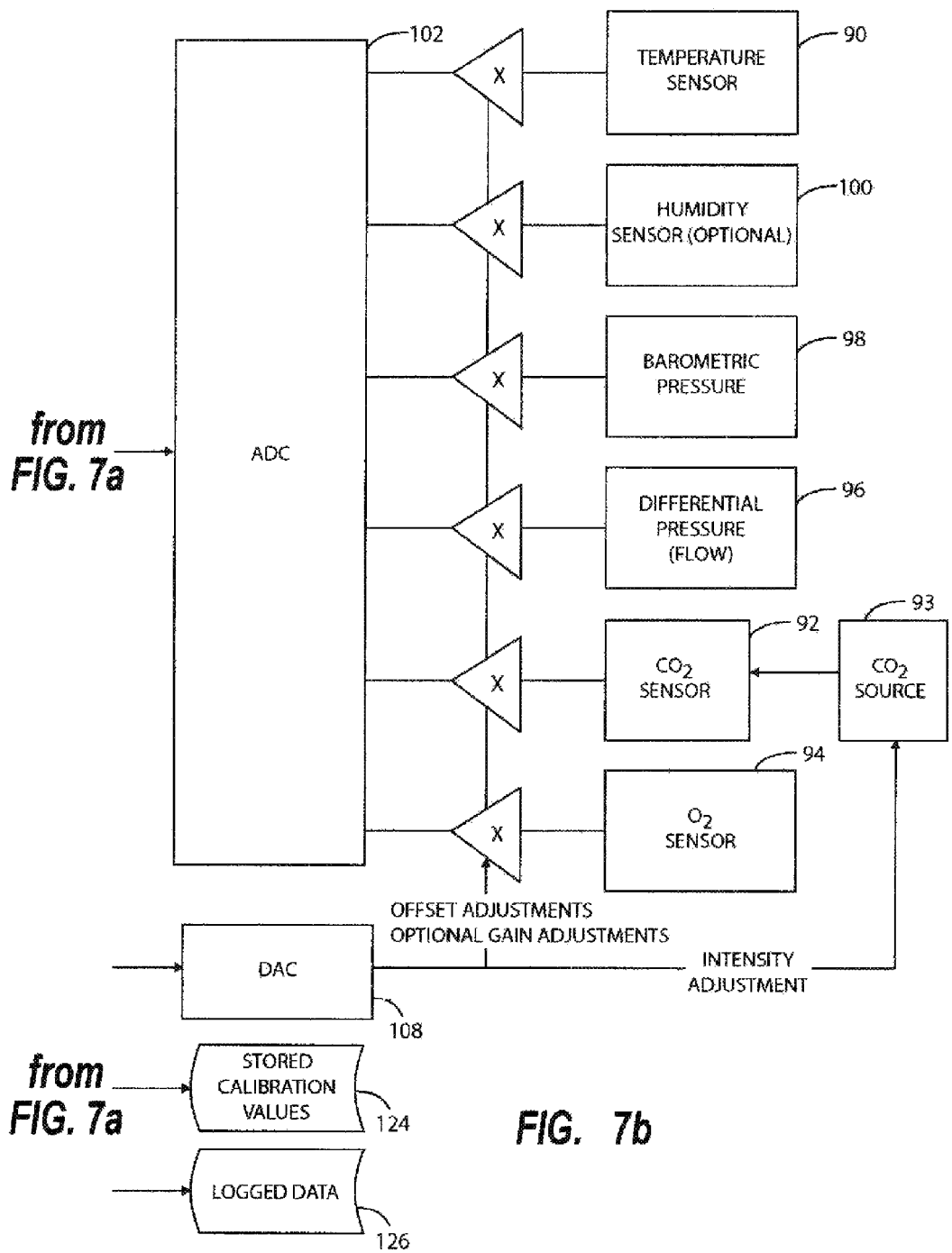

The microcontroller 104 preferably includes a serial channel digital input pin 110 to which heart rate information is delivered from a body contacting electrode by way of a wireless link represented by block 112 in FIG. 7. Computed results from the microcontroller may be presented directly over a USB cable 114 to a personal computer 116 or by way of a "Bluetooth" wireless connection represented by block 118.

The batteries 24 (FIG. 2) are preferably of the rechargeable type and are connected through a charger 120 to a power distribution link 122 connected to supply DC voltage to the microcontroller 104, the amplifiers (X), the analog-to-digital converter 102, the digital-to-analog converter 108, the sensors, and to an electrically erasable PROM. The direct PC connection 116 connects to the battery charging circuit 120, via the USB port on the PC, and provides the power required. Software within the memory of the microcontroller 104 oversees the power management to control the charger and to control the power going out to the several circuits driven by the DC power supply 122. The power/battery management routines are used to minimize the battery drain by entering a "sleep mode" if the system is inactive.

Calibration values for the $CO_2$ sensor and the $O_2$ sensor are adapted to be stored in a flash memory 124 and, similarly, computed test results upon a person may be stored in an EEPROM memory 126 mounted on the digital printed circuit board 80 of FIG. 6.

As mentioned earlier, the IR source in the bore 50 (FIG. 4) is typically a low wattage (less than about 500 mw) incandescent light bulb is able to emit infrared light in a spectrum to which IR detector 56 is responsive. The light is made to traverse a selected one of the three semicircular, open light guides 62 contains respired gas, and because $CO_2$ in the respired gas absorbs infrared light, a signal proportional to the concentration of $CO_2$ in the respired gas is produced at the output of the $CO_2$ detector 92. The arcuate curvature increases the path length and improves the sensitivity of the $CO_2$ detector. As already mentioned, while only one such arcuate path as at 62 is used at any given time, the others provide symmetry to the flow path through the device 10 and to insure more reliable differential pressure measurements by the sensor 96. Also, by having redundant paths, by simply rotating the member 34 (FIG. 2), a new arcuate path can have its endpoints aligned with the IR source and sensor, i.e., substituted for one possibly becoming contaminated and less light reflective.

Mainstreaming systems need frequent and accurate re-calibration procedures as they operate in an environment where filtration, temperature and pressure control, vibration and shock suppression are not an option. Many tests can take as long as thirty minutes, therefore it is necessary to carry out calibrations without interruption of the main flow of information.

The method used to calibrate the $O_2$ and $CO_2$ sensors as described in the Howard et al. patent application Ser. No. 11/899,335, filed Sep. 5, 2007, and entitled "Gasless Calibration of Metabolic analyzer transducer" may be employed. The content of the application is hereby incorporated by reference in its entirety. In the method, at the time of factory setup, the lamp comprising the $CO_2$ source is dimmed to produce the same change in detector output resulting when a test gas of a known concentration of $CO_2$ is made to flow. This provides for automatic calibration of the output of the $CO_2$ detector in the field without the need to have a calibration gas or a reference cell on hand. Instead, a constant, indicative of a voltage decrease applied to the lamp source corresponding to the IR absorption produced by a known test gas established at the factory, is stored in the memory 124 and is employed at the time of field calibrations. Real-time calibration of the $CO_2$ sensor, using the ambient inspiration time in which auto-calibration occurs, allows the $CO_2$ detector to be spanned on every breath to correct for drift from temperature variations and light guide contamination. Zeroing is also achieved on every breath at low ventilation rates up to 60 breaths-per-minute.

In operation, the three main sensing systems-flow (via differential pressure), oxygen, and carbon dioxide all have an interrelation dependency. Their relative response times and attenuation can be aligned to give meaningful integration of the expired gas concentrations.

Because of this dependency, one can start the calibration procedure somewhere, and in the present invention, we start with the carbon dioxide signal. Regardless of its calibration, this sensor produces an entidal waveform during the expired phase, followed by an immediate reversal of signal at the onset of inspiration due to the influx of ambient air over the sensor. Obviously the inspired phase has already commenced at the time the sensor undergoes this signal change and this time period is a function of:

1) The volume downstream of the sensor
2) The rate of inspiration
3) The time constant of the sensor
4) The diffusion constant of the expired and inspired gases.

This can be reduced to a simple calculation which predicts the time delay in milliseconds of the response of the sensor to the actual point of crossover between expired and inspired flow or zero flow. This information allows for one method of flow zeroing the pressure sensor. However, it provides for a very accurate point to determine when the oxygen and carbon dioxide sensors have been fully flushed with incoming ambient air. At this point, the oxygen sensor can be spanned and the CO2 sensor zeroed.

From the time of change of CO2 signal and as a function of the breath repetition rate, this point can be accurately determined. The point being time-based is affected by the breathing rate because at rest (12 BPM) the time delay would be in the order of 2.5 seconds. Conversely at 60 BPM, the time delay would only be 0.5 seconds. The breath repetition rate is provided by the flow sensor.

Volume measurement is achieved by measuring the pressure drop across the base 66 of the optical guide 34 containing the critical orifice 64. The microprocessor-based controller 104 computes an output which is proportional to the square root of the signal from the differential pressure transducer 96 and is linear with respect to flow.

Without limitation, a LM 61 temperature sensor may be used in implementing the temperature sensor 90 to measure the inspired/expired gas temperature. Oxygen consumption and carbon dioxide delivery are standardized to standard temperature (0° C.), barometric pressure at sea level (101.3 κPa (and dry gas (STPD))). Humidity sensing employs an optional sensor 100 may be used for calculating ambient oxygen values during a calibration sequence. Ambient oxygen (20.93% dry) is a direct function of temperature and absolute humidity.

The 12-bit A/D converter 102 provides resolution of oxygen and carbon dioxide values to +/−0.01% and minute ventilation ranging from 2-140 liters with a resolution of better than 0.1 liters.

The thus described assembly of the housing and all of its internal components weighs less than 5 ounces and has a volume of about 50 cubic inches. As such, it can be removably affixed to a facemask covering the nose and mount using a Velcro hook and loop fastener or button-like coupling between stand-off buttons on the base member 18 and buttonholes in the facemask.

Figure 8A:
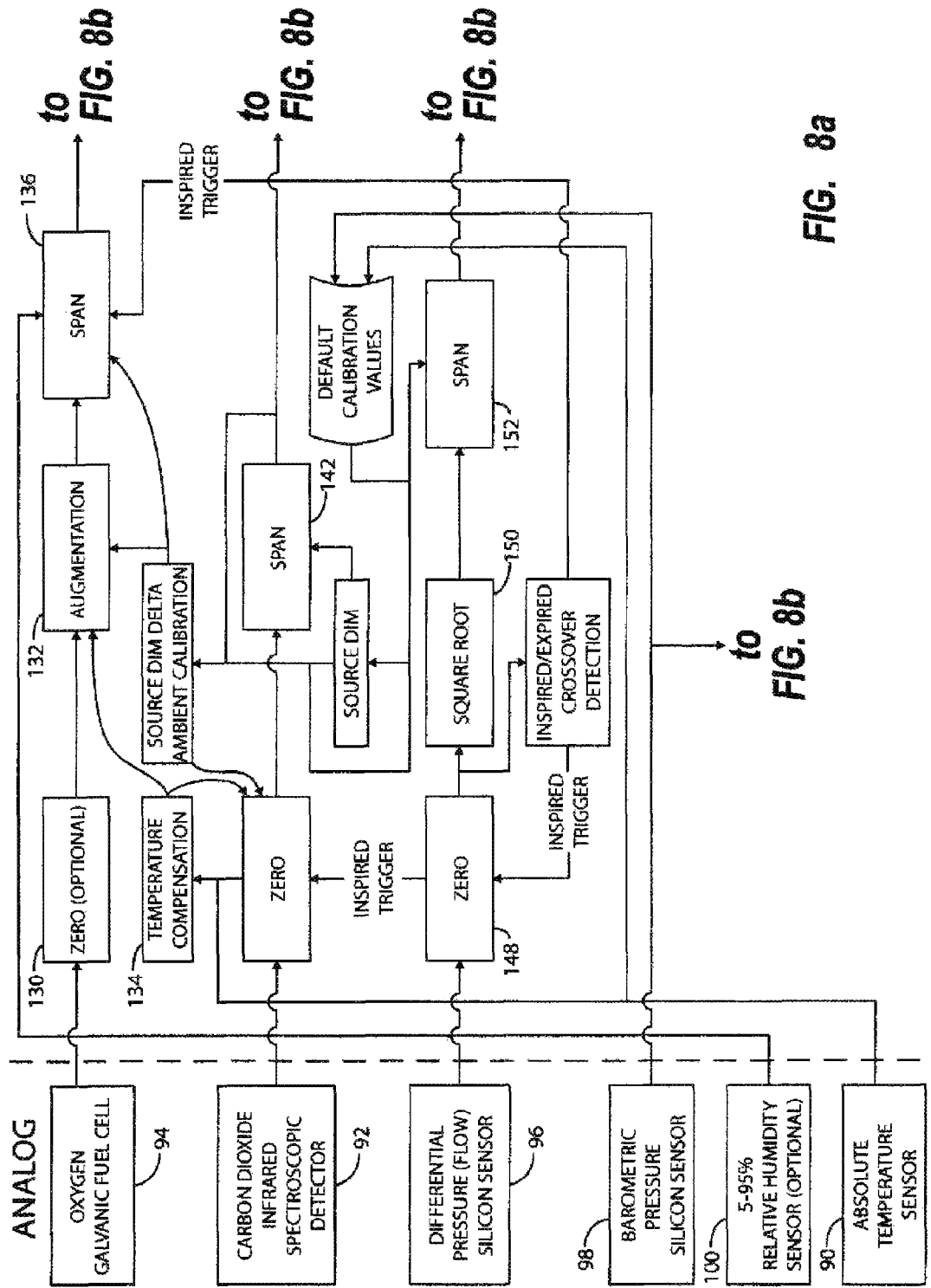
FIG. 8 is a further block diagram illustrating the signal processing and computational steps executed by the microcontroller embodied in the metabolic analyzer transducer of the present invention.
Figure 8B:
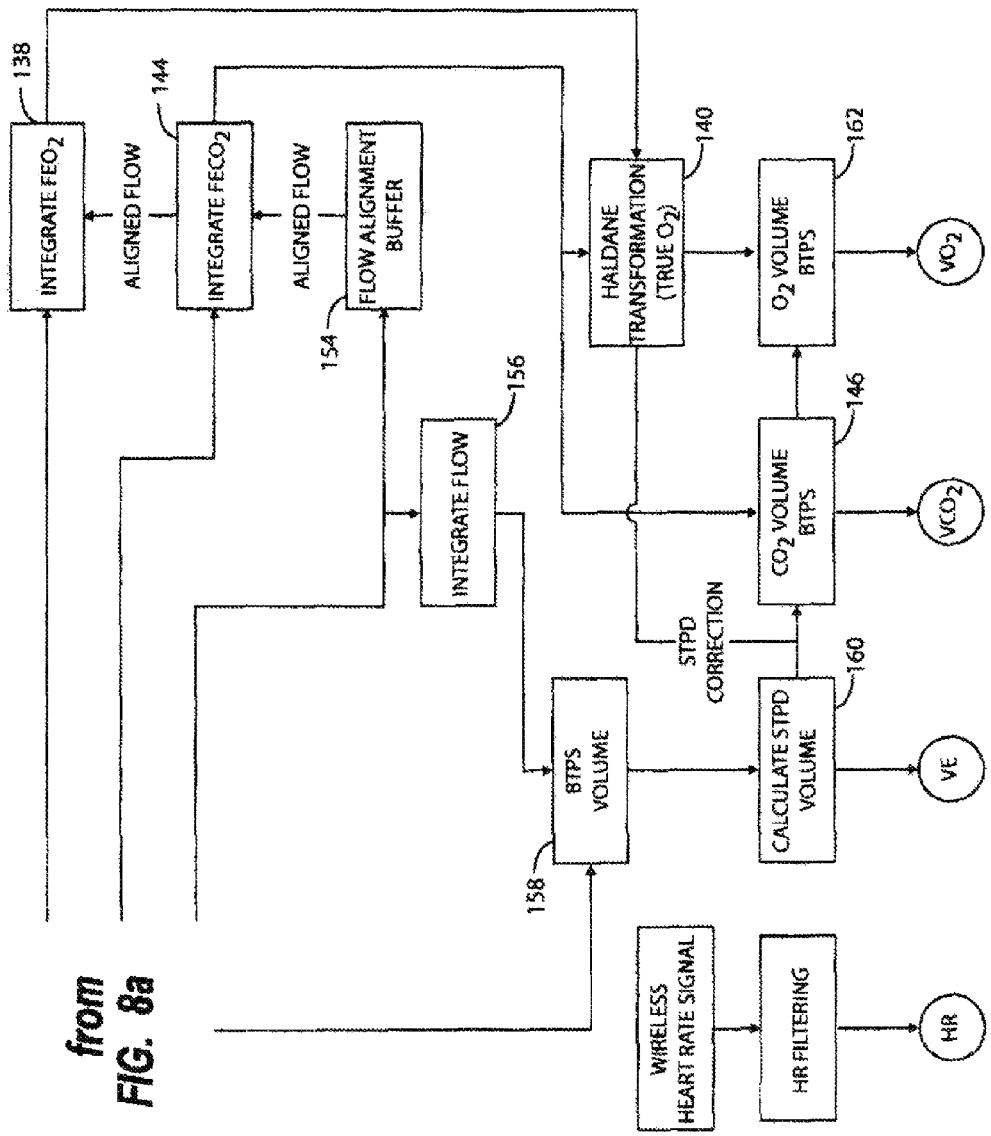

Turning next to FIG. 8, there is illustrated by means of a block diagram the signal processing and computational steps executed by the microcontroller 104. The "ANALOG" section on the left of the vertical dashed line corresponds with at the right side of FIG. 7 showing the several sensors/detectors and the different signals coming into the microcontroller via the A/D converter 102. Most of the digitized sensor signals require a "zero", i.e., an offset adjustment. For example, starting with the oxygen sensor 94 in FIG. 8 following zeroing at block 130, the next function performed by the microcontroller's processor is "augmentation" (block 132), which is basically an extrapolation routine where the slope of the input signal is examined and an estimate is made where the signal will arrive at, based on the steepness of the slope. Stated otherwise, the steeper the signal's slope, the augmentation routine ends up calculating a higher $O_2$ and then, as the $O_2$ signal gets close to its maximum point, the slope begins dropping off and becomes the read value.

Also affecting the augmentation operation is a temperature compensation operation 134. The temperature compensation step takes the value from the absolute temperature sensor 90 to make an adjustment to the oxygen concentration reading based upon measured temperature.

For the oxygen sensor, it can be assumed an ambient oxygen concentration is based on humidity and temperature. From relative humidity and temperature, absolute humidity, as a percentage of the ambient, can be established. Knowing 20.93% is the oxygen concentration of dry air, the actual oxygen concentration can be established. The oxygen sensor has an absolute zero so once the span is established, this linear detector provides accurate oxygen analyses. However, the response of the oxygen sensor is inherently too slow to follow the changes in oxygen seen in expired breath and to react to the change of oxygen during the inspired phase having a time constant (T90) of 400 milliseconds. The oxygen signal's response is therefore augmented using a first derivative algorithm from the expression:

$$V_{out} = \frac{V_{t0} - V_{t1}}{\Delta t} K$$

This provides a T90 response in the order of 150 milliseconds. The galvanic cell oxygen sensor used is a partial pressure sensor so the effect of pressure on oxygen concentrations, expressed as a percentage, can be corrected. The analyzer of the present invention is a mainstream device, the oxygen sensor is exposed directly to the breath and the pressure drop across the orifice plate, which is used to measure the flow, provides a measure of pressure at the $O_2$ sensor's cathode. As the $O_2$ sensor is mounted at the orifice plate, the actual pressure is the differential pressure divided by 2. To compensate for the change in oxygen, the following pressure correction factor is determined with the following equation:

$$p_{cor} = \frac{p_a}{p_a \cdot \frac{p_\Delta}{2}}$$

$P_{cor}$=Pressure Correction Factor
Where: $p_a$=Ambient Pressure
$P_\Delta$=Pressure drop across orifice Before this correction is used, it can be slowed to match the natural response of the sensor so the correction can be carried out. This 'slowing' is achieved using a digital RC network. The expression for this correction is:

$$\alpha = \frac{\Delta t}{RC + \Delta t} \text{ and } y_n = \alpha x + (1 - \alpha) x$$

Once the correction is carried out, the oxygen signal can be augmented as described earlier.

Another factor influencing the augmentation step 132 is based on the zero and span adjustments of the $CO_2$ detector 92. In operation of the device of the present invention, the $CO_2$ signal has a faster response time compared to the $O_2$. Hence, it has been found expedient in developing the augmentation for the proper use of calibration factors referencing the response time of the $CO_2$ sensor.

The carbon dioxide detector is zeroed at the point in the inspired phase as previously described when ambient air is present. The CO2 level in the ambient air has a large effect on signal, especially as the non-linear output defined by the Beer-Lambert law accentuates this effect at higher measured CO2 levels. The ambient level is established by dimming the IR source at two levels. One representative of 5% CO2 and the other 0.1% CO2. The level of output achieved at the 5% CO2 equivalence is normalized to a default value stored by the microcontroller 104. This default value was established with an actual ambient level of 1000 ppm CO2 (0.1%) at the time of factory set-up. The difference in output change between the two dimming levels is a direct function of the departure from linearity caused by an ambient level other than 0.1% and the actual level can be calculated. The line extended through this value provides the true zero of the sensor. Since ambient levels change slowly, this value is applied at each inspiratory point during a test.

Because of contamination of the optical guide, occlusion on the detector window or temperature variation, it is necessary to span the carbon dioxide detector every few breaths. This is achieved by immediately dimming the source equivalent to a 5% CO2 change at the change of signal at the end of the endtidal waveform and reading the actual CO2 reading at the previous established point at the end of the inspiratory phase. Comparing this to the default value in RAM and correcting for any changes in atmospheric pressure allows for the CO2 signal to be spanned. The dimming of the source and its return to normal operating levels takes typically 800 milliseconds. Power augmentation of the source by overdriving it to the two required levels brings this time down to 400 milliseconds. This method minimizes the interruption to the data stream although some inaccuracy of reading can be expected in the breath immediately following this routine.

The temperature of the CO2 detector case can remain stable while measuring the voltage output. Any change of case temperature will cause a change in the output of the detector regardless of the intensity of the light delivered through the optical light path. Since the infrared source and detector are in close proximity and installed in common aluminum housing 48, the block of aluminum is heated by the source and is transferred to the case of the detector. Dimming the source reduces the temperature delivered to the case of the CO2 detector along with the intensity of light delivered through the optical guide. This effectively reduces detector output voltage because of two independent causes. This causes an error when trying to measure only the intensity change of the light. To steady the voltage output, a method has been invented to counterbalance the temperature change caused by dimming the source. Specifically, a second infrared source not part of the optical path, but has been installed alongside the primary source, is used. The primary source heats as a by-product of the light created and effectively heats the case of the CO2 detector. When the primary source dims and the total power delivered is reduced, the second source is turned on to ensure the total power delivered is equivalent. The net result is equivalent heat provided to the CO2 case even when the primary source dims. This allows us to detect only the light intensity change delivered to the detector through the optical guide.

An alternative method is to provide real time calibration coincidental with the data stream. This is achieved by applying a 50 Hz oscillation to a specially designed, low wattage source and measuring the peak-to-peak values of the detector output. The IR source (bulb or emitter) only draws 30 ma and has a high speed time constant. The detector may be a TO18 package with a typical time constant of 12 milliseconds. Changes in this peak-to-peak value, after correction for pressure, when compared to the default value, allows for instantaneous calibration of signal. Power augmentation of the source and first derivative augmentation of the detector maximizes the signal response. See FIG. 8. This is a very powerful calibration method as it removes changes in output over the course of the breath which may be due to condensation in the light guide or occlusion due to saliva etc.

Following augmentation, a span function is performed on the $CO_2$ signal. See block 136. As reflected in FIG. 8, the oxygen span operation is dependent upon temperature, relative humidity and an "inspired trigger" which is required because both inspired and expired $O_2$ are of interest. It is known, with inspired air, oxygen concentration is nominally at 20.93% dry but then calculated as function of relative humidity, allowing the inspired breath to assure a detected signal goes back down to its baseline. The augmented and gain adjusted oxygen value is then integrated (box 138) to yield the fractional expired oxygen ($FEO_2$).

The microcontroller 104 is programmed to execute the so-called "Haldane Transformation" whereby inspired $O_2$ concentration is multiplied by the ratio of expired to inspired $N_2$ leading to the calculation of the inspired oxygen volume. It takes both the oxygen and the carbon dioxide values and ends up calculating the amount of oxygen is consumed. See block 140 in FIG. 5.

Consider next the signal processing taking place on the carbon dioxide signal. A zeroing operation, taking into account temperature compensation, a change due to source dimming and an inspired trigger, permits accurate zeroing and for an inspired breath, $CO_2$ concentration is low. In performing the "span" on the $CO_2$ signal (box 142), the IR source is dimmed by a known amount, as previously explained, allowing recalculation of the span factor. Integrating the span adjusted quantity (box 144) yields total carbon dioxide production for a given breath (box 146).

Because the integrity of the flow signal is vital to accurate metabolic measurements, auto zeroing of the differential pressure transducer is very helpful as small changes in zero create a large error in the waveform alignment for integration of the oxygen and CO2 signals. All pressure sensors have a small amount of drift due to temperature and the square root of the signal is being used, the voltages dealt with are very small. Transducers are compensated for temperature changes and additional compensation is added by reading the ambient temperature and adding additional correction based thereon. Even so some zero correction is necessary on long tests or when the environment is extreme or changeable. In order to detect when the flow is truly at zero, the endtidal CO2 value is used as a point when there is a flow reversal and a correction to zero on the next breath is applied. This assumes there has been no major physiological change from one breath to the next.

An alternative method which uses the inherent microphony of the pressure sensor as an advantage will now be discussed. Bonded strain gauge transducers employ a very thin silicon diaphragm which flexes with pressure. When there is either a positive or negative pressure imparted on the membrane, noise, which can be introduced onto the diaphragm from outside sources, such human voice, vibration, wind flow, etc. is reduced to a minimum. However at the point of rest this noise level increases. By monitoring and filtering the peak to peak noise levels, the noise associated with the zero flow condition can be isolated. By adjusting the zero so this noise is equally distributed either side provides a novel way of zeroing the pressure transducer. The noise is measured in 'counts'. Span changes on this type of pressure sensor are negligible and therefore there is no need to calibrate them.

Considering next the differential pressure (flow) sensor 96, a zeroing operation first takes place at block 148 with the inspired trigger providing a dynamic adjustment for drift or the like in the sensor 96. The properly zeroed signal is then subjected to a square root operation 150 operative to convert the differential pressure measurement to a flow value. The span operation 152 provides a multiplier to obtain a correct output value operated on by the flow alignment buffer 154 allowing the $CO_2$ and $O_2$ to be properly aligned with the flow on a breath-by-breath basis.

Mention is made of the barometric pressure, temperature, and humidity sensors. These three all play a major role in enhancing and correcting the performance of the flow, CO2 and oxygen sensors. The aforementioned devices are inherently stable and if used with quality instrument amplifiers have no drift in either zero or span for life.

The barometric pressure sensor 98 along with an integration of the flow signal (box 156) is used to develop body temperature and pressure saturated volume (box 158). From this, the volume at body temperature saturated with water vapor can be calculated (block 160) yielding the subjects minute ventilation (VE).

The computed value of fractional expired $O_2$ ($FEO_2$) from block 138 when subjected to Haldane transformation (block 140) and multiplied by the standard temperature and pressure, dry (STPD) volume yields the volume of $O_2$ absorbed in a given breath at STPD. The STPD correction factor applied to block 162 yields the oxygen uptake $VO_2$ in liters/minute. Likewise, applying the STPD correction to the computation reflected by block 146 yields the value of $CO_2$ production ($VCO_2$).

The present invention provides a first of a metabolic analyzer transducer sufficiently small and lightweight to be worn as an attachment to a facemask such as described in U.S. Pat. No. 6,718,982 and has an NDIR $CO_2$ sensor accurately measuring $CO_2$ concentration in expired air on a breath-by-breath basis on a subject undergoing a physical workout.

Figure 9:
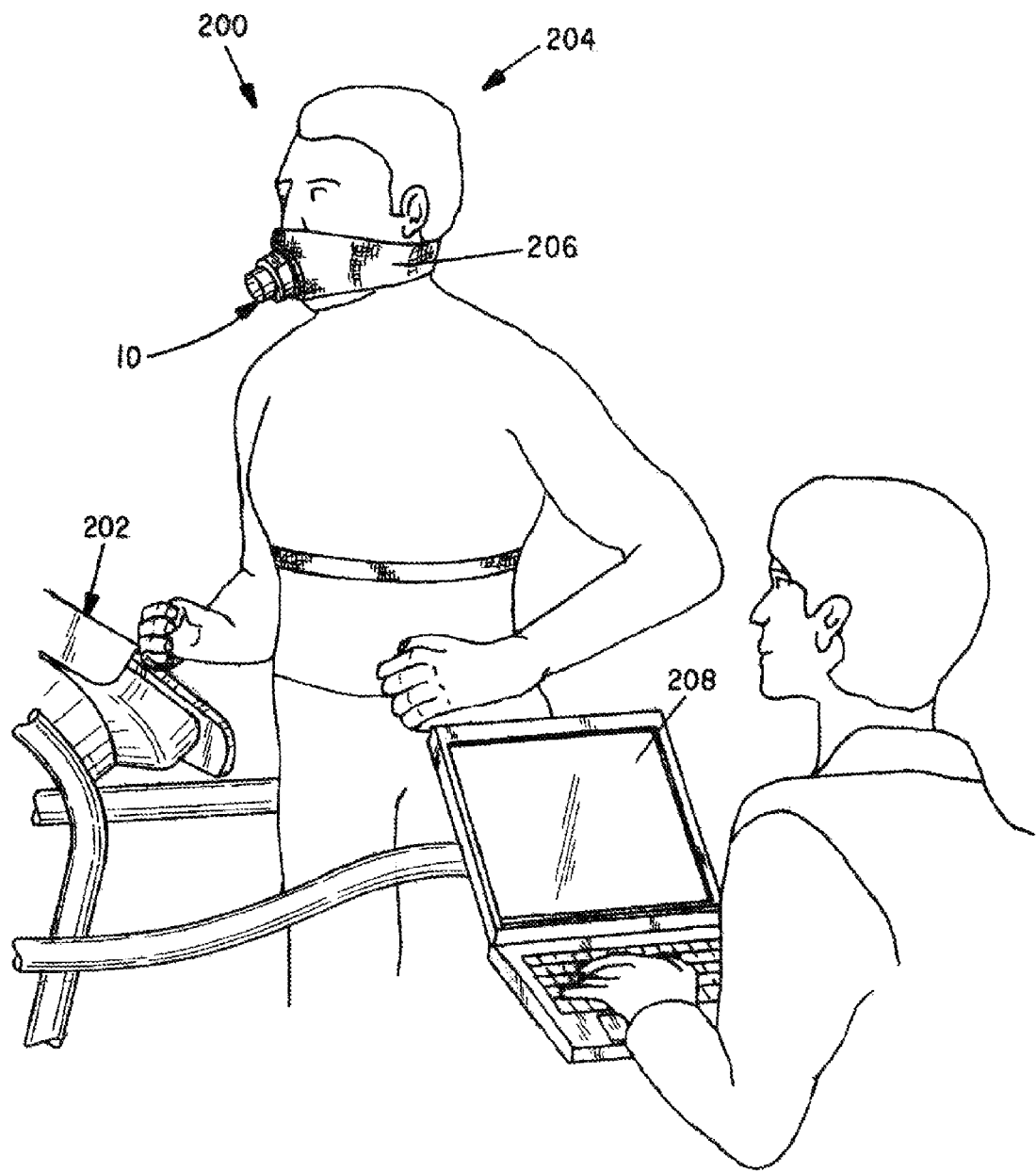
FIG. 9 is a perspective view of a metabolic analyzer transducer system in embodiment of the present invention.

With reference to FIG. 9, a perspective view of a metabolic analyzer transducer system in embodiment of the present invention is shown. A metabolic analyzer transducer system is generally shown at 200 having an ergometer 202, a subject 204, a facemask 206 coupling a metabolic analyzer transducer 10, a user interface 208.

Ergometer 202 can be most any device increasing the subject's metabolism. Ergometer 202 can be a treadmill as shown in FIG. 9 or an elliptical machine, a stair machine, a stationary or non-stationary bike, or even a swimming pool. It is fully contemplated ergometer 202 could be most any type of device without departing from the spirit of the invention. Further, it is fully contemplated ergometer 202 would not be needed. For example, metabolic analyzer transducer 10 would still operate well if subject 204 was out for a jog sans a treadmill.

Facemask 206 can be adapted to be worn on the face of a subject covering the subject's nose and mouth. Formed through the thickness dimension of mask 206 is an aperture through which transducer 10 can be inserted. The aperture is positioned so as to align with the subject's mouth when mask 206 is being worn. To provide support for transducer 10, it has been found expedient to utilize a soft rubber grommet stretched to receive the outside surface of transducer 10 through the center opening thereof and whose outside diameter forms a zero clearance fit with the aperture formed in the mask 206. Alternatively, to provide more rigid support for Transducer 10 in certain applications, a flexible plastic strip is inserted between two layers of mask material. This plastic strip supports an interface plate to which a plate with three spools on Transducer 10 attaches firmly. The three spools, one of which is on a different PCD provides the correct orientation of the transducer Facemask 206 can be formed from Lycra™ fibers woven as a spandex fabric, allowing it to stretch and conform closely to the contour of the subject's face with very little, if any, dead space between the inside surface of facemask 206 and the subject's face. To make facemask 206 better conform to the bridge of the subject's nose, it has been found convenient to provide a soft malleable metal clip riveted to the mask.

It is noted facemask 206 can readily support transducer 10 due to the transducer's size (e.g., less than 10 cubic inches) and weight (e.g., between 10 to 3 oz. and hopefully less than 5 oz.). As discussed above in great detail, metabolic analyzer transducer 10 is anon-invasive, lightweight, small mainstream metabolic analyzer transducer providing output signals corresponding to a subject's respiratory exchange ration on a real-time, breath-by-breath basis.

User interface 208 can be most any interface displaying information transmitted to it by wireless connection device 118 or through direct PC connection 116 through a wireless connection. User interface 208 can be a PC as shown in FIG. 9 or user interface 208 can be a PDA (personal digital assistant), a cell phone, watch, or any device capable of communication utilizing Bluetooth™ technology or other similar wireless networks (e.g. ANT™). Metabolic information relayed from transducer 10 can be presented through a graphical user interface as shown in FIG. 9. By presenting the information on a cell phone, PDA, or other small electronic device, subject 206 is able to see a breath-by-breath output of his or her metabolic variables. This would allow the subject to try and get the most out of a workout or even an evaluation of their health.

Thus, embodiments of the METABOLIC ANALYZER TRANSDUCER are disclosed. One skilled in the art will appreciate the present teachings can be practiced with embodiments other than those disclosed. The disclosed embodiments are presented for purposes of illustration and not limitation, and the present teachings are limited only by the claims follow.

What is claimed is:

1. A unitary lightweight analyzer comprising, in combination:
   (a) a housing having a tubular socket with a central lumen;
   (b) an oxygen sensor mounted to the housing and exposed to the lumen for producing a first electrical signal proportional to inspired and expired oxygen;
   (c) a diatomic gas sensor contained in the housing including an arcuate, open channel having a concave wall with a reflective surface thereon and first and second ends, the first end aligned with an IR source and the second end aligned with an IR detector for producing a second electrical signal proportional to the concentration of a predetermined gas in inspired and expired respiratory air flowing through the transducer;
   (d) a flow sensor exposed to respiratory gas flow in the lumen for producing a third electrical signal proportional to the respiratory gas flow, the oxygen sensor, diatomic gas sensor and the flow sensor aligned with a mainstream respiratory gas flow path through the lumen;
   (e) an analog-to-digital converter connected to receive the first, second and third electrical signals; and
   (f) a microcontroller circuit coupled to the analog-to-digital converter, said oxygen sensor, diatomic gas sensor, flow sensors, analog-to-digital converter and microcontroller circuit being contained in a housing of a size and weight is adapted to be supported on the face of a subject whose oxygen uptake and carbon dioxide production are to be measured.

2. The unitary lightweight analyzer as in claim 1 wherein said housing comprises;
   (a) an outer shell having a first wall, a second wall and a side wall joining the first wall to the second wall and defining a hollow chamber and where the second wall and first wall each include a centrally disposed aperture;
   (b) a detector mounting structure contained in the hollow chamber, the detector mounting structure having a base with a central aperture concentrically aligned with the apertures in the first wall and second wall and with the tubular socket projecting outward of the base; and (c) an optical waveguide member dimensioned to fit within said tubular socket, the optical waveguide member having a tubular sidewall and a base, the tubular sidewall containing said arcuate, open channel and the base having an orifice of a predetermined shape and size, and where a portion of the tubular sidewall of the optical waveguide member extends through the aperture in the first wall.

3. The unitary lightweight analyzer as in claim 2 wherein the arcuate open channel comprises a reflective surface and is exposed to respiratory air made to flow through the aperture in the second wall.

4. The unitary lightweight analyzer as in claim 3 wherein the IR source is operatively positioned to inhibit moisture condensation on the reflective surface.

5. The unitary lightweight analyzer as in claim 2 wherein the oxygen sensor comprises a galvanic fuel cell is disposed in a holder joined to the tubular socket of the detector mounting structure and is exposed to respiratory air made to flow through the aperture in the bottom wall.

6. The unitary, lightweight analyzer as in claim 2 wherein the flow sensor includes an electronic pressure sensor operatively disposed on opposite sides of said base of the optical waveguide member and configured to measure a pressure drop across the base due to air flow through said orifice in the base of the waveguide member.

7. The unitary lightweight analyzer as in claim 2 and further including an absolute temperature sensor affixed to the detector mounting structure and exposed to respiratory air passing through the tubular socket, past the detector mounting structure and through the optical waveguide member.

8. The unitary lightweight analyzer in claim 2 wherein the analog-to-digital converter is mounted on a first printed circuit substrate disposed in a first space between the outer shell and the tubular socket of the housing.

9. The unitary lightweight analyzer as in claim 8 and further including a second printed circuit substrate having the microcontroller circuit affixed thereto, the second substrate being disposed in a second space between the outer shell and the tubular socket of the housing.

10. The unitary lightweight analyzer as in claim 9 and further including a power supply disposed in the housing and operatively coupled to the analog-to-digital converter and the microcontroller circuit.

11. The unitary lightweight analyzer as in claim 10 wherein the power supply disposed in the housing is operatively coupled to the IR source and the IR detector.

12. The unitary lightweight analyzer as in claim 11 wherein the IR source is an incandescent lamp.

13. The unitary lightweight analyzer as in claim 10 wherein the power supply comprises a battery disposed in said housing and operatively coupled to the flow sensor, the IR source, and the IR detector.

14. The unitary lightweight analyzer as in claim 2 wherein said housing and contents weigh less than 5 oz.

15. The unitary lightweight analyzer as in claim 1 and further including a wireless transmitter disposed in the housing and coupled to the microcontroller circuit for sending computed values of oxygen uptake and carbon dioxide production to a remote receiver.

16. The unitary lightweight analyzer as in claim 1 and further including a serial data input channel on the microcontroller adapted to receive heart rate signals from an external heart rate sensor over a wireless communications link.

17. A lightweight respiratory gas concentration analyzer comprising, in combination:

(a) a tubular housing having a respiratory gas flow channel extending from a proximal end to a distal end of said housing; and (b) a diatomic gas detector module adapted to measure $CO_2$ concentration disposed in said housing in alignment with the gas flow channel, said detector module having an optical waveguide member with an arcuate, open groove with a concave wall, the concave wall having a reflective surface thereon for steering optical energy along a curved path and said groove having first and second ends, the first end aligned with an IR source and the second end aligned with an IR detector, the open groove adapted to receive samples of inspired and expired air from a subject on whom the transducer is attached.

18. The lightweight respiratory gas concentration analyzer of claim 17 and further including an oxygen sensor mounted on the detector module and exposed to respiratory gas flowing through the gas flow channel.

19. The lightweight respiratory gas concentration analyzer of claim 18 and further including a flow sensor in the housing for measuring the volume rate of flow of respiratory gas through the flow channel.

20. The lightweight respiratory gas concentration analyzer of claim 19 and further including a temperature measuring device and a barometric pressure sensor affixed to the housing.

21. The lightweight respiratory gas concentration analyzer of claim 20 and further including a dc power supply disposed in the tubular housing for providing power to the IR source, the IR detector, the oxygen sensor and the temperature sensor.

22. The lightweight respiratory gas concentration analyzer of claim 21 and further including a microcontroller disposed in the housing and connected to the IR source, the IR sensor, the oxygen sensor, the temperature sensor, the dc power supply, the flow sensor and the barometric pressure sensor for computing the subject's oxygen uptake and carbon dioxide production on a breath-by-breath basis.

23. The lightweight respiratory gas concentration. analyzer of claim 22 and wherein said microcontroller includes a serial communication channel comprising a transceiver disposed in said housing for communication with a remote computer.

24. The lightweight respiratory gas concentration analyzer of claim 22 wherein the microcontroller controls the intensity of the IR source.

25. The lightweight respiratory gas concentration analyzer of claim 17 wherein the reflective surface comprises a thin film of gold deposited on the concave wall.

26. A metabolic analyzer system, comprising:
a metabolic analyzer transducer including means for sensing $CO_2$ production by a subject and means for sensing $O_2$ content of inspired and expired respiratory gases;
a facemask for supporting and operably coupling the metabolic analyzer transducer to the subject; and
a user interface communicatively coupled to the metabolic analyzer transducer.

27. The metabolic analyzer system of claim 26, further comprising an ergometer.

28. The metabolic analyzer system of claim 27, wherein the user interface and ergometer are contained in one device.

29. The metabolic analyzer system of claim 28, wherein the ergometer is a stationary bicycle.

30. The metabolic analyzer system of claim 27, wherein the ergometer can be any one of a treadmill, elliptical machine, stair machine, bike, cross or a country trainer.

31. The metabolic analyzer system of claim 26, further comprising a wireless connection device housed on the metabolic analyzer transducer for communicatively coupling the metabolic analyzer transducer with the user interface.

32. The metabolic analyzer system of claim 31, wherein the wireless connection device is a Bluetooth wireless transceiver.

33. The metabolic analyzer system of claim 26, wherein the facemask can support 5 oz or less.

34. The metabolic analyzer system of claim 26, further comprising a microcontroller housed in the metabolic analyzer transducer capable of receiving inputs from the $CO_2$ sensor.

35. A method of manufacturing a metabolic analyzer transducer, comprising the steps of:
(a) molding an outer plastic shell having a bottom wall, a top wall and a side wall joining the top wall to the bottom wall and defining a hollow chamber where the bottom wall and top wall each include a centrally disposed aperture;
(b) placing a detector mounting structure in the hollow chamber, the detector mounting structure having a base with a central aperture concentrically aligned with the apertures in the top wall and bottom wall and with a tubular socket projecting outward of the base; and
(c) inserting an optical waveguide member within said tubular socket, the optical waveguide member having a tubular sidewall and a base containing an arcuate, open channel and an orifice of a predetermined shape and size in the base, and where a portion of the tubular sidewall of the optical waveguide member extends through the aperture in the top wall.

36. The method of claim 35, further comprising the step of inserting an oxygen sensor for producing a first electrical signal proportional to inspired and expired oxygen into the central aperture.

37. The method of claim 36, further comprising the step of attaching a diatomic gas sensor to the detector mounting structure, the diatomic gas sensor including said arcuate, open channel said channel having a concave wall with a reflective surface thereon and first and second ends, the first end aligned with an IR source and the second end aligned with an IR detector for creating a non-linear optical path between the IR source and the IR detector and for producing a second electrical signal proportional to the concentration of a predetermined gas in inspired and expired respiratory air flowing through the orifice.

38. The method of claim 37, further comprising the step of attaching a flow sensor to the detector mounting structure, the flow sensor producing a third electrical signal proportional to a pressure drop across said orifice, the oxygen sensor, diatomic gas sensor and the flow sensor aligned with a mainstream respiratory gas flow path.

39. The method of claim 38, further comprising the step of coupling an analog-to-digital converter to the detector mounting structure, the analog-to-digital converter connected to receive the first, second and third electrical signals.

40. The method of claim 39, further comprising the step of coupling a microcontroller circuit to the detector mounting structure, the microcontroller circuit coupled to the analog-to-digital converter, said oxygen sensor, diatomic gas sensor, flow sensors, and analog-to-digital converter.

41. The method of claim 40, wherein the metabolic analyzer is of a size and weight adapted to be supported by a facemask to be worn by a subject whose oxygen uptake and carbon dioxide production are to be measured.

42. The method of claim 41, wherein the arcuate open channel is exposed to respiratory air made to flow through the aperture in the bottom wall.

43. The method of claim 42 wherein the oxygen sensor comprises a galvanic fuel cell disposed in a holder joined to the tubular socket of the detector mounting structure and is exposed to respiratory air made to flow through the aperture in the bottom wall.

44. The method of claim 43 wherein the flow sensor includes electronic pressure sensors operatively disposed on opposite sides of said base of the optical waveguide member and configured to measure a pressure drop across the base due to air flow through said orifice in the base of the waveguide member.

45. A method of manufacturing a lightweight respiratory gas concentration analyzer comprising, comprising the steps of:
(a) molding a tubular housing having a respiratory gas flow channel extending from a proximal end to a distal end of said housing; and
(b) placing a diatomic gas detector module in said housing in alignment with the gas flow channel, said detector module having a non-linear optical waveguide member comprising an arcuate, open groove with a concave wall, the concave wall having a reflective surface thereon for conveying IR energy through the arcuate, open groove and said groove having first and second ends, the first end aligned with an IR source and the second end aligned with an IR detector, the open groove adapted to receive samples of inspired and expired air along its length from a subject on whom the transducer is attached.

46. The method of claim 45 further comprising the step of mounting an oxygen sensor on the detector module and exposing to respiratory gas flowing through the gas flow channel.

47. The method of claim 46 further comprising the step of forming an orifice in a base of the optical waveguide member for measuring a pressure drop across said base due to gas flow through said orifice.

48. The method of claim 47, further comprising the step of affixing a temperature measuring device and a barometric pressure sensor to the housing.

49. The method of claim 48, further comprising the step of inserting a dc power source in the tubular housing for providing power to the electronics and sensors.

50. The method of claim 49, further comprising the step of inserting a microcontroller in the housing.

51. The method of claim 50, further comprising the step of connecting the microcontroller to the IR source, the IR sensor, the oxygen sensor, the temperature sensor, the dc power supply, the flow sensor and the barometric pressure sensor for computing the subject's oxygen uptake and carbon dioxide production on a breath-by-breath basis.

52. The method of claim 51, wherein the microcontroller includes a serial communication channel comprising a transceiver disposed in said housing for communication with a remote computer.

53. The method of claim 52, wherein the microcontroller controls the intensity of the IR source.

54. The method of claim 53, wherein he reflective surface comprises a thin film of gold deposited on the concave wall.

55. A method of measuring a metabolic rate of a subject, comprising the steps of:
measuring the concentration of $CO_2$ in a respiratory gas stream with an analog sensor located within a housing coupled to a facemask; measuring air flow with a flow sensor located within the housing;
receiving inputs from the analog sensor at a microcontroller and computing $CO_2$ production by the subject, the microcontroller located within the housing; zeroing a flow transducer during each breath; and powering the analog sensor and microcontroller with a power source located within the housing operatively coupled to the microcontroller and analog sensor.

56. The method of claim 55, further comprising the step of measuring $O_2$ with an $O_2$ sensor located within the housing.

57. The method of claim 56, further comprising the step of transmitting measured physiological values of the subject with a wireless transmitter located within the housing.

58. The method of claim 56, further comprising the step of transferring physiological values of the subject to a remote device via a wireless connection.

59. The method of claim 55, further comprising the step of measuring respired air from the subject with a respiratory gas analyzer located within the housing.

60. The method of claim 59, further comprising the step of measuring temperature with an absolute temperature sensor located within the housing.

61. The method of claim 55, further comprising the step of zeroing $CO_2$ measurement.

62. The method of claim 61, further comprising the step of spanning $O_2$, on a breath by breath basis.

63. The method of claim 62, further comprising the step of correcting an $O_2$ signal from flow to yield a pressure compensated $O_2$, output.

64. The method of claim 63, further comprising the step of augmenting the $O_2$ signal to provide real-time breath by breath measurements and removal of DC drift.

* * * * *